(12) United States Patent
Glynn

(10) Patent No.: US 9,289,666 B2
(45) Date of Patent: Mar. 22, 2016

(54) BASEBALL TRAINING APPARATUS

(71) Applicant: Eugene P. Glynn, Waseca, MN (US)

(72) Inventor: Eugene P. Glynn, Waseca, MN (US)

(*) Notice: Subject to any disclaimer, the term of this patent is extended or adjusted under 35 U.S.C. 154(b) by 0 days.

(21) Appl. No.: 14/268,664

(22) Filed: May 2, 2014

(65) Prior Publication Data

US 2015/0273304 A1    Oct. 1, 2015

Related U.S. Application Data

(63) Continuation-in-part of application No. 13/970,591, filed on Aug. 19, 2013, now Pat. No. 8,747,260, and a continuation of application No. 13/024,257, filed on Feb. 9, 2011, now Pat. No. 8,512,172.

(51) Int. Cl.
  *A63B 69/00* (2006.01)
  *A63B 69/36* (2006.01)
  *A61F 9/04* (2006.01)
  *A63B 71/10* (2006.01)

(52) U.S. Cl.
  CPC ............. *A63B 69/0002* (2013.01); *A61F 9/045* (2013.01); *A63B 69/00* (2013.01); *A63B 69/002* (2013.01); *A63B 69/3608* (2013.01); *A63B 71/10* (2013.01); *A63B 2069/0006* (2013.01); *A63B 2069/0008* (2013.01); *A63B 2102/18* (2015.10); *A63B 2225/09* (2013.01)

(58) Field of Classification Search
  CPC .. A63B 69/00; A63B 69/002; A63B 69/3608; A61F 9/045
  USPC ........... 473/458, 422, 450, 464, 59, 208, 210; 2/12; 434/247, 252
  See application file for complete search history.

(56) References Cited

U.S. PATENT DOCUMENTS

| | | | | | |
|---|---|---|---|---|---|
| 673,789 | A | * | 5/1901 | Ricketts | 417/257 |
| 1,585,023 | A | * | 5/1926 | Fant | 2/13 |
| 1,628,551 | A | * | 5/1927 | Noyes | 2/12 |
| 3,144,658 | A | * | 8/1964 | Byron | 351/44 |
| 3,613,116 | A | * | 10/1971 | Stroup | 473/450 |
| 3,660,852 | A | * | 5/1972 | Schulenberg | 2/12 |
| 4,298,991 | A | * | 11/1981 | Recenello | 351/47 |
| 4,969,649 | A | * | 11/1990 | Lugiewicz | 473/210 |
| D359,977 | S | * | 7/1995 | Taber et al. | D16/315 |
| 5,877,837 | A | * | 3/1999 | Hayes | 351/44 |
| 7,048,371 | B1 | | 5/2006 | Moore | |
| 7,322,693 | B2 | * | 1/2008 | Abraham | 351/44 |
| 8,157,663 | B1 | | 4/2012 | Winkelsas et al. | |
| 8,512,172 | B1 | * | 8/2013 | Glynn | 473/458 |
| 8,747,260 | B1 | * | 6/2014 | Glynn | 473/458 |
| 2014/0026301 | A1 | | 1/2014 | Brown | |

\* cited by examiner

*Primary Examiner* — Mitra Aryanpour
(74) *Attorney, Agent, or Firm* — Albert W. Watkins

(57) ABSTRACT

A baseball training apparatus occludes peripheral vision of each eye across the nose region of a baseball player by creating a visual divide that extends from and immediately adjacent to the nose along the central sagittal plane. In various embodiments, the visual divide is extendible, removable and replaceable, pivotal, and may incorporate scribes to vary shape or geometry. The visual divide may further be mounted from a pair of glasses without lenses, though other embodiments with and without lenses are contemplated. The eye divider is used to align or confirm alignment of a baseball player properly with the pitcher, to ensure that the batter has both eyes facing the pitcher.

8 Claims, 10 Drawing Sheets

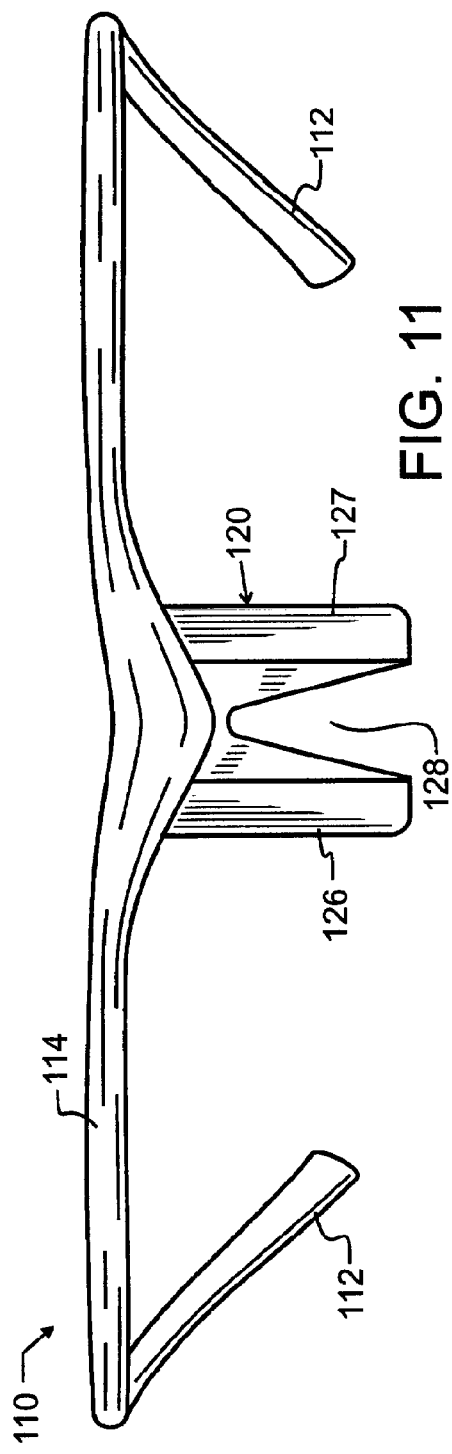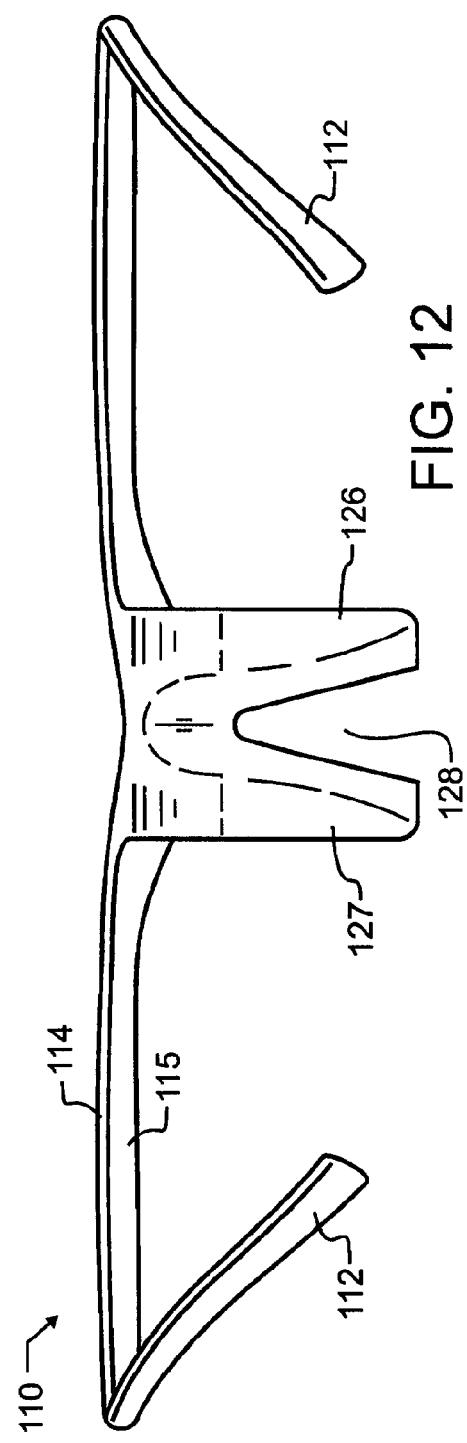

BASEBALL TRAINING APPARATUS

CROSS REFERENCE TO RELATED APPLICATIONS

The present application is a Continuation-In-Part of co-pending U.S. application Ser. No. 13/970,591 filed Aug. 19, 2013 and presently allowed, which is in turn a continuation of U.S. application Ser. No. 13/024,257 filed Feb. 9, 2011 and granted on Aug. 20, 2013 as U.S. Pat. No. 8,512,172, the contents of each which are incorporated herein by reference in entirety.

BACKGROUND OF THE INVENTION

1. Field of the Invention

This invention pertains generally to games using tangible projectiles, and more particularly to a player worn baseball training apparatus and associated methods.

2. Description of the Related Art

In the sport of baseball, a player's first or early lesson will be to stand sideways to a pitcher, with shoulders generally lined up to the pitcher. This stance is foreign to many first-time participants, and instead many of those participants will naturally try to face the pitcher. While facing the pitcher inhibits proper swinging motion, and so is frowned upon, a player will preferably face their head to the pitcher. By doing so, the player will gain full benefit of binocular vision, and will best read and respond to changes in pitch and ball flight. Unfortunately, for most beginning players, facing their head to the pitcher while turning their shoulders askance is very unnatural. As a result, proper posture is hard to teach. Additionally, over time even the most skilled players may unintentionally and unknowingly alter their stance. In many cases, the dominant eye of a batter is their back eye. A right handed person who bats right handed will also typically be right eye dominant, and their right eye will be the back eye. If they do not face the pitcher, not only will they lose the benefit of binocular vision, they will be tracking the pitcher and pitched ball with their weaker eye. Unfortunately, there is no apparatus or method available for such players to better facilitate their learning, improvement, or verification of proper stance.

There have been a number of blinders, eye shields, or training devices developed for other sports such as golf, bowling and tennis which are intended to facilitate training and concentration. Exemplary patents and published applications, the teachings and contents which are incorporated herein by reference, include U.S. Pat. No. 2,433,590 by Barr, entitled "Golfer's eyeshield"; U.S. Pat. No. 2,825,065 by Spiezio, entitled "Blinker-equipped spectacles for bowlers"; U.S. Pat. No. 3,868,108 by Kirchner, entitled "Athletic training device"; U.S. Pat. No. 4,168,111 by Baines, entitled "Golfing glasses"; U.S. Pat. No. 4,969,649 by Lugiewicz, entitled "Performance enhancement apparatus"; U.S. Pat. No. 5,050,982 by Meissner, entitled "Method and apparatus for improving visual acuity"; U.S. Pat. No. 5,171,152 by McCleery, entitled "Training device for batters and golfers"; U.S. Pat. No. 5,177,510 by Peters et al, entitled "Alignment eyeglasses"; U.S. Pat. No. 5,661,534 by Gill, entitled "Peripheral vision limiting visor"; U.S. Pat. No. 5,800,278 by Varriano, entitled "Apparatus for signaling proper alignment of user's eye and object to be struck"; U.S. Pat. No. 7,322,693 by Abraham, entitled "Focus-enhancing blinders"; Des 359,977 by Taber et al, entitled "Eye shields for bowling"; WO9100541 by Peters et al, entitled "Alignment eyeglasses"; and WO9850118 by Varriano, entitled "Sports training apparatus".

Additionally, there are inventions developed for driving that prevent glare and distraction, illustrated by the following US patents, the contents and teachings which are incorporated herein by reference: U.S. Pat. No. 1,505,882 by Geiger, entitled "Driving glasses"; U.S. Pat. No. 1,577,700 by Edwards, entitled "Vision deflector"; U.S. Pat. No. 1,653,139 by Westgaard et al, entitled "Eyeshade for auto drivers"; U.S. Pat. No. 1,660,993 by Gales, entitled "Eye protector for vehicle drivers"; U.S. Pat. No. 1,685,725 by Rowe, entitled "Spectacles"; U.S. Pat. No. 1,801,406 by Woodmansee, entitled "Antiglare goggles"; U.S. Pat. No. 1,844,232 by Tharp, entitled "Glare shield for personal wear"; U.S. Pat. No. 1,907,356 by Klein, entitled "Antiglare shield"; U.S. Pat. No. 1,953,320 by Thomas, entitled "Eye protector"; U.S. Pat. No. 2,870,446 by Mitchell, entitled "Pilot's instrument flying hood"; U.S. Pat. No. 3,226,729 by Fucci, entitled "Eye shield"; and U.S. Pat. No. 5,877,837 by Hayes, entitled "Side view mirror glare reduction device".

Light shades, serving more generic purpose, the contents and teachings which are incorporated herein by reference, include: 673,786 by Ricketts, entitled "Shaded eyeglasses"; U.S. Pat. No. 1,471,967 by Mahlmann, entitled "Eye shade"; U.S. Pat. No. 1,574,144 by White, entitled "Eye shade"; U.S. Pat. No. 1,585,023 by Fant, entitled "Antiglare eye protector"; U.S. Pat. No. 2,176,006 by Ehrlich, entitled "Eyeshield"; U.S. Pat. No. 2,224,560 by Wentz, entitled "Eyeshade means"; and U.S. Pat. No. 2,541,242 by Grove, entitled "Eyeshield".

Sun shield nose protectors, the contents and teachings which are incorporated herein by reference, include: U.S. Pat. No. 1,048,191 by Maurice, entitled "Sun shield for the nose"; U.S. Pat. No. 2,197,973 by Everett et al, entitled "Nose protector"; and U.S. Pat. No. 5,666,664 by Hamilton, entitled "Face protector shade". Some other patents, the contents and teachings which are incorporated herein by reference, include: U.S. Pat. No. 1,252,126 by Letzeisen, entitled "Spectacles", which describes collapsible glasses; U.S. Pat. No. 3,421,233 by Gaal, entitled "Vision training device and method for achieving parallel sightings", which describes a reading training device; and U.S. Pat. No. 5,647,835 by Martineau, entitled "Method for preventing motion sickness", which describes an apparatus to prevent motion sickness.

These aforementioned patents provide a wide variety of glasses and the like which solve a number of diverse problems. Unfortunately, none serve to adequately address the needs of a baseball player trying to determine or optimally adjust his viewing position.

In addition to the foregoing patents, Webster's New Universal Unabridged Dictionary, Second Edition copyright 1983, is incorporated herein by reference in entirety for the definitions of words and terms used herein.

SUMMARY OF THE INVENTION

In a first manifestation, the invention is a baseball training apparatus for assisting a baseball player in keeping their head aligned with an object. A frame defines a forward portion of said baseball training apparatus and extends longitudinally between distal ends substantially within a coronal anatomical plane to define top and bottom generally planar major surfaces. A pair of temples each extend generally perpendicularly from one of the distal ends of the frame body support and are adapted to operatively couple the baseball training apparatus to baseball player. An eye divider is coupled with and extends from the frame bottom generally planar major surface, and has right and left dividers separated by a small gap at a first termination distal to the frame that converge adjacent to the frame. The small gap is adapted to operatively couple about a nose bridge of the baseball player such that the nose bridge will operatively extend into the small gap. The eye divider is adapted to operatively define a central sagittal plane of a baseball player, and is also adapted to operatively extend from immediately adjacent to the baseball player's nose and thereby adapted to operatively divide a baseball player's eyes, remain immediately adjacent to the baseball player's nose, and remain substantially within the baseball player's central sagittal plane. In a further manifestation, the frame has a slight curvature out of the coronal plane that is adapted to operatively provide slight but important controlled flexure in the event of a direct baseball impact.

In a second manifestation, the invention is a method of confirming visual alignment of a baseball player during batting so that both right and left eyes of the baseball player are facing in sight of a pitcher. According to the method, peripheral vision is occluded within each of the right and left eyes to create two perceived images of the visual divide by the steps of: occluding vision in a coronal plane above said right and left eyes; extending a visual divide generally centered between right and left eyes first defined by a nose on a player's face away from adjacent to the nose and generally parallel to a central sagittal plane of the baseball player and from said vision occluding coronal plane downward therefrom to block sight of a pitcher and baseball that would otherwise cross adjacent to the player's nose; and retaining the visual divide extension in abutment with the player's nose and generally parallel to the central sagittal plane of the baseball player. In a further step according to the method, a perceived image of at least one of the pitcher and baseball is centered between the two perceived images of the visual divide extension.

OBJECTS OF THE INVENTION

Exemplary embodiments of the present invention solve inadequacies of the prior art by providing an eye divider similar to the nose, but extending therefrom. In one preferred embodiment, the eye divider is pivotally mounted from a pair of glasses without lenses, though other embodiments with and without lenses are contemplated. The eye divider is used to align or confirm alignment of a baseball player properly with the pitcher, to ensure that the batter has both eyes facing the pitcher.

The present invention and the preferred and alternative embodiments have been developed with a number of objectives in mind. While not all of these objectives are found in every embodiment, these objectives nevertheless provide a sense of the general intent and the many possible benefits that are available from embodiments of the present invention.

A first object of the invention is to provide an apparatus and method for enhancing baseball training. A second object of the invention is to enable the apparatus to be adjustable to players of very diverse sizes and characteristics. Another object of the present invention is to provide an apparatus that is safe to use, and, preferably, durable enough to be transported about in a duffel bag or the like. A further object of the invention is to provide an apparatus and method that are intuitive to players of all skill levels and experience, and which will help them to align with the pitcher. Yet another object of the present invention is to provide an apparatus that may be easily fabricated for low cost.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which:

FIG. 11 illustrates the third preferred embodiment baseball training apparatus of FIG. 9 from a front elevation view.

FIG. 12 illustrates the third preferred embodiment baseball training apparatus of FIG. 9 from a rear elevation view.

DESCRIPTION OF THE PREFERRED EMBODIMENT

Manifested in the preferred embodiment, the present invention provides an eye divider 20 similar to a player's nose 4, but extending therefrom. In the preferred embodiment, eye divider 20 is generally planar, has a large surface area relative to thickness, and extends generally along or parallel to the sagittal anatomical plane to divide the player's face into right and left halves. Eye divider 20 is pivotally mounted from a frame resembling a pair of glasses without lenses, though other embodiments are contemplated. The eye divider 20 is used to align or confirm alignment of a baseball player 1 properly with the pitcher, to ensure that the player 1 has both eyes 2, 3 facing directly at the pitcher.

Figure 1:
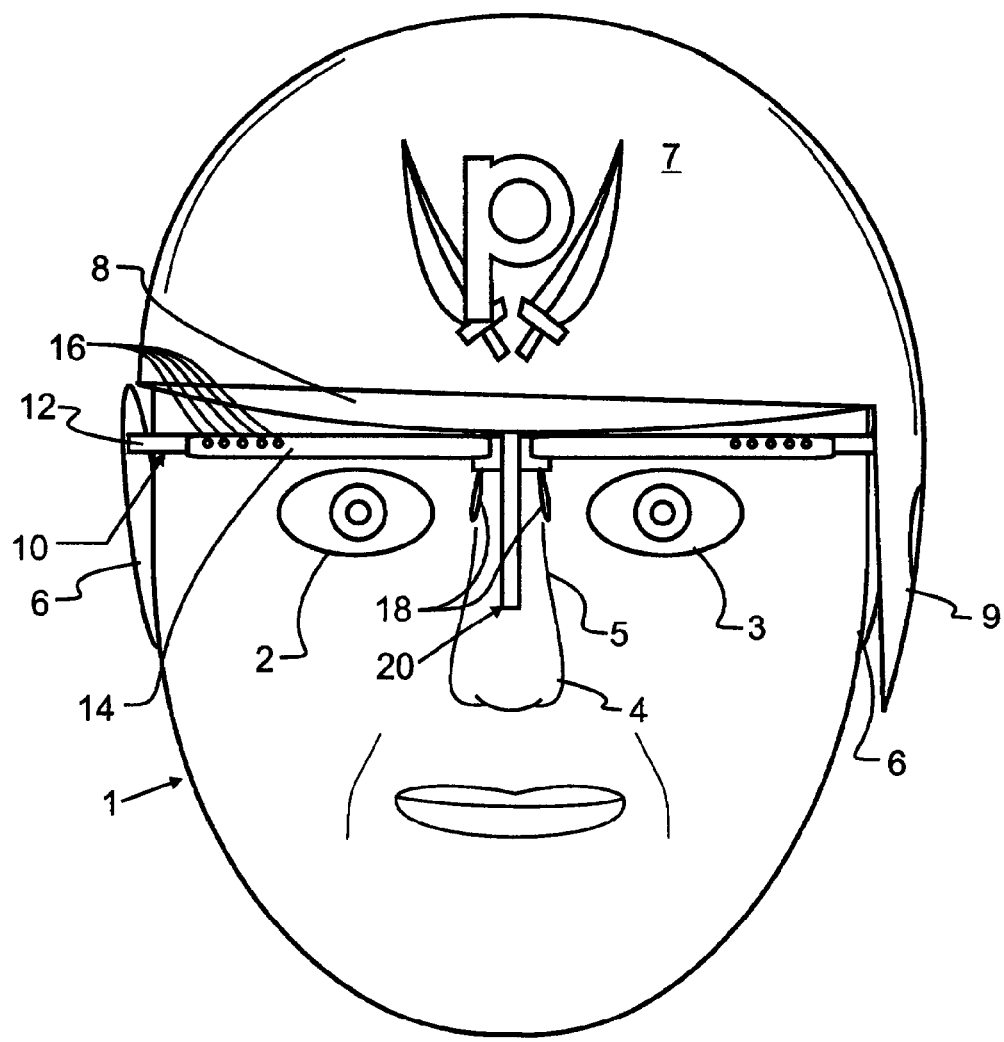
FIG. 1 illustrates a first preferred embodiment baseball training apparatus designed in accord with the teachings of the present invention from a front elevation view.

As illustrated in FIG. 1, an exemplary prior art baseball player 1 has vision from right eye 2 and left eye 3. Player 1 has a nose 4 that extends to the bridge region 5 between right eye 2 and left eye 3. One or both of left and right ears 6 may be covered by a protective extension 9 extending from protective baseball helmet 7. Helmet 7 will also typically include a visor 8 that provides shade from the sun. Prior art player 1 is additionally wearing a first preferred embodiment baseball training apparatus 10 designed in accord with the teachings of the present invention, including a pair of temples or legs 12, left and right frame top bar members 14, and eye divider 20. To couple temples 12 with top bar members 14, at least one protrusion will optionally be provided that extends from each temple 12 and engages within ones of the plurality of holes 16 formed through top bar members 14.

By providing a plurality of holes 16, and preferably two protrusions extending from each temple 12, temples 12 may be press-fit to top bar members 14 at one of several different positions, allowing temples 12 to be moved closer together or spaced farther from each other. This adjustability allows the baseball training apparatus 10 to be set for different users without having to measure and custom fabricate a baseball training apparatus 10 for each baseball player 1. Alternatively, temples 12 may be coupled through standard hinges to top bar members 14 as is taught in the art of eyeglasses and incorporated by reference herein above, or may have other detachable or permanent connection there between.

In either the case of adjustable or fixed coupling between temples 12 and top bar members 14, temples 12 may further be fabricated from a resilient material, and be provided with sufficient curvature that the ends of temples 12 distal to top bar members 14 are closer to each other than the ends adjacent. This combination of the free ends of temples 12 being closer together and providing resilience in temples 12 allows the temples to gently squeeze or hold on a person's head. Good materials selection and design may eliminate the need for adjustable connection through holes 16. In such case, it is further contemplated that the preferred baseball training apparatus 10 might, for exemplary purposes only and not limiting the present invention thereto, be provided in only a few sizes, such as a child's size and an adult size, where differences of wearers within the size ranges are fully accommodated by the resilience of temples 12.

Nose piece 18 is preferably designed to rest on nose bridge region 5, and together with temples 12 support the balance of baseball training apparatus 10 upon baseball player 1, preferably in a position as generally illustrated in FIG. 1. Nose piece 18 may take on any of the many geometries known in the glasses art, and the present invention is not limited by one or another design.

Figure 2:
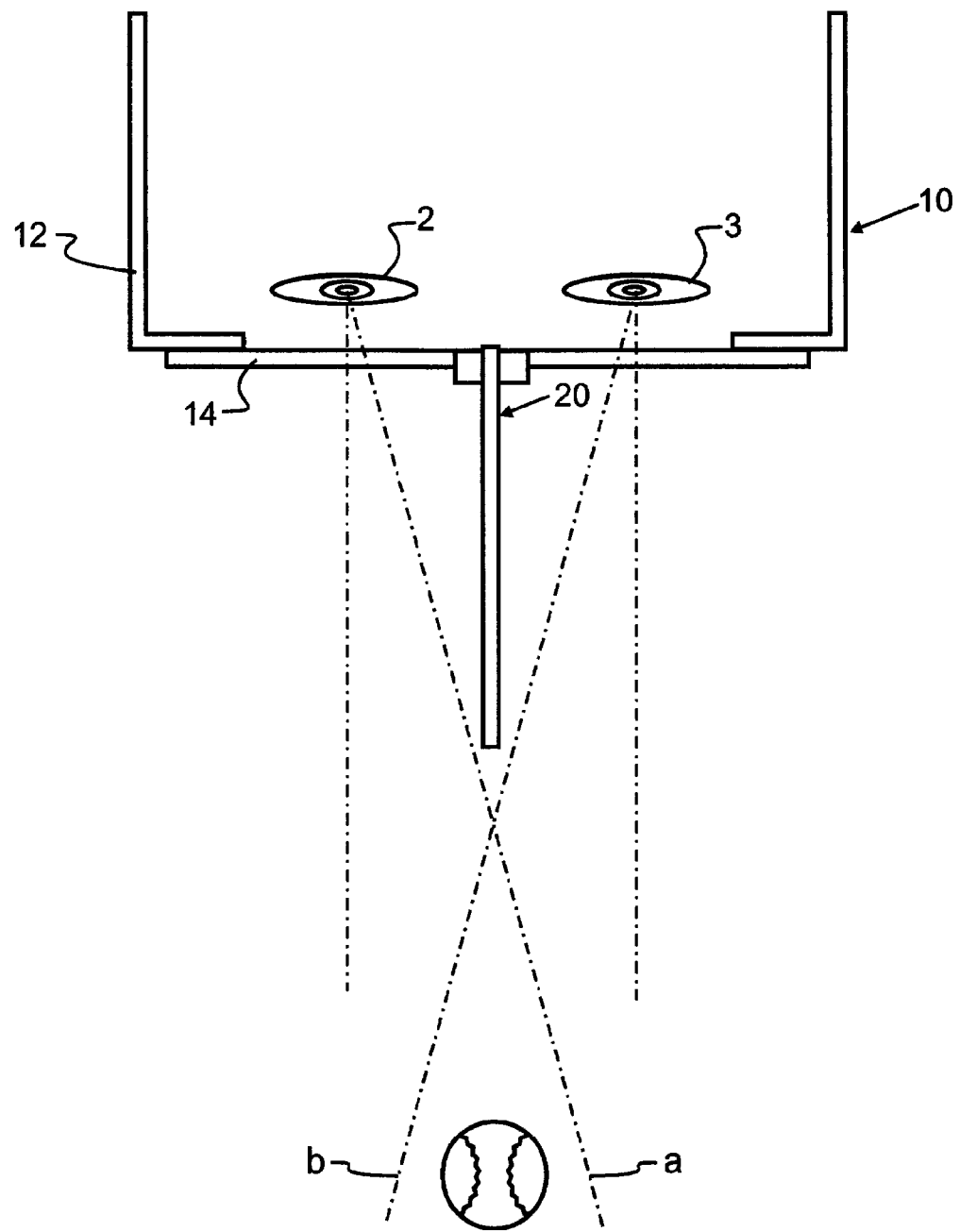
FIG. 2 illustrates the first preferred embodiment baseball training apparatus of FIG. 1 from a top, simplified or schematic view.

FIG. 2 illustrates baseball training apparatus 10 from above, using a very simplified or schematic view to illustrate the operation thereof. A baseball player 1 will most desirably position so that right eye 2 and left eye 3 are facing directly at a pitcher or incoming baseball. To enable baseball player 1 to confirm that eyes 2, 3 are, in fact, directly facing the pitcher, baseball training apparatus 10 is placed on the player's face as shown in FIG. 1. If right eye 2 in FIG. 2 were to be closer to the pitcher or incoming baseball than left eye 3, then the farthest right line of sight from left eye 3, designated by line b in the figure, would become blocked by eye divider 20, such that the baseball or pitcher would no longer be visible through left eye 3. Similarly, if player 1 has his head shifted the other direction, then the baseball or pitcher would no longer be visible through right eye 2 along leftmost line of sight a.

Alternative training methods are contemplated herein that are facilitated by baseball training apparatus 10. According to a first method, eye divider 20 may extend away from the player's nose 4 by a relatively small amount. In this case, eye divider 20 would not fully block the view of the pitcher. Instead, player 1 will try to balance the view of eye divider 20, while keeping the pitcher or ball centered. In this position, eye divider 20 will appear to be both to the left of and to the right of the ball or pitcher. This signifies to player 1 that his head is pointed in the desired direction. If not, then player 1 will need to rotate his head to center the ball or pitcher between the two perceived eye dividers. Noteworthy here is that if eye divider 20 is sufficiently small, the image of the divider may actually seem to disappear, just as a person's nose is usually not noticed during ordinary activities. While for most persons their nose is, in fact, visible, the image is sufficiently unobtrusive to go unnoticed when they are looking directly at an object.

According to a second method, eye divider 20 extends farther from nose 4, and player 1 will simply ensure that the ball or pitcher is visible from both right eye 2 and left eye 3. While this may seem to be the simpler or more preferred method, it is actually not. The larger size of eye divider 20 may result in eye divider 20 becoming too obtrusive and interfering with play. Depending upon materials used, eye divider 20 may also be more readily damaged, either when in use or during transit. Surprisingly, a relatively small eye divider 20 in conjunction with the first method will work well for most players.

According to a third method, baseball training apparatus 10, regardless of the length eye divider 20 extends away from the nose, is only placed upon player 1 briefly, so that player 1 can check for proper stance and posture prior to actually batting. Once stance and posture are confirmed, then player 1 will remove baseball training apparatus 10 for actual batting. This third method is compatible with both the first and second methods of training, and so may be used therewith as desired.

Not all players will have the same nose geometry, yet, preferably, eye divider 20 will be placed or positioned immediately adjacent to nose 4. A gap there between can allow a batter to see with the back eye between eye divider 20 and nose 4, thereby rendering eye divider 20 ineffective or less beneficial. For the purposes of the present disclosure, eye divider 20 will be understood to be immediately adjacent to nose 4 when any gap there between is sufficiently small to substantially prevent clear or unobstructed vision there between.

One variable that can impact this gap, and so is preferably addressed, is the slope of the top-facing surface of the nose. As may be understood, at nose piece 18, the distance between eye divider 20 and nose 4 can be precisely controlled. However, slope of nose 4 will affect the distance there between undesirably, if eye divider 20 and nose 4 do not share a common slope. To accommodate the varying geometries of noses, eye divider 20 is preferably mounted to top bar members 14 through a pivoting coupling 30 visible in FIG. 3. This figure also illustrates eye divider 20 in a clockwise extreme rotation relative to temples 12. FIG. 4 illustrates eye divider 20 in a counterclockwise extreme rotation relative to temples 12.

Figure 5:
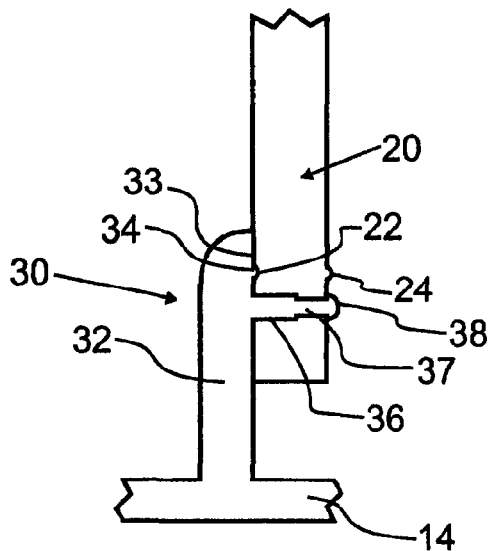
FIG. 5 illustrates an exemplary coupling between eye divider and frame from a sectional view.

FIG. 5 illustrates pivoting coupling 30 through a cross-sectional view, showing an exemplary coupling between eye divider and top bars 14. Coupling body 32 is fixed in position relative to top bars 14, and includes a generally planar, washer-shaped bearing surface 33. Protruding out of the center of bearing surface 33 is bushing 36, retention neck 37, and head 38. The combination of bearing surface 33, bushing 36, retention neck 37, and head 38 securely capture eye divider 20, such that eye divider 20 may simply be pressed over head 38, where it will be captured and be pivotal. Eye divider 20 will rotate about an axis of rotation that is parallel to the longitudinal direction of neck 37, the axis of rotation which is also normal to bearing surface 33.

Eye divider 20 will also most preferably not rotate freely, but will instead incorporate some form of resistance with bearing surface 33, bushing 36, retention neck 37, and head 38 which impedes rotation except when player 1 intentionally manipulates eye divider 20. This may be accomplished a number of ways. For exemplary purposes only, and not limiting thereto, one or more small, discrete hemispherical bumps 34 may be provided that protrude slightly from the surface of bearing surface 33. In this exemplary manifestation, one or more matching hemispherical indentations 22 are provided in eye divider 20. As eye divider 20 is rotated, bumps 34 will fall into indentations 22, which will tend to discourage further rotation of eye divider 20. Only when sufficient force is generated to pull bumps 34 out of indentations 22 will eye divider 20 be rotated further. If eye divider 20 is made from a semi-rigid or rigid sheet material, then indentations 22 may be formed by punching eye divider 20 at appropriate lactations, which will in turn form small bumps 24 on the opposite face of eye divider 20.

While detents formed by bumps 34 and indentations 22 illustrate one method of preventing unintended or unwanted rotation of eye divider 20, many other techniques are contemplated and considered incorporated herein. For exemplary purposes only, and again not limiting the present invention solely thereto, geometries and materials that form friction between pivoting coupling 30 and eye divider 20 may also be used to gain equivalent result. For example, eye divider 20 may be fabricated from a semi-rigid foam material such as rubber or polyurethane. Additionally or alternatively, the regions of eye divider 20 and pivoting coupling 30 that engage with each other may have a rough finish rather than a smooth finish or may have a high co-efficient of friction rather than being slippery. In yet another alternative, a material having a high static co-efficient of friction, such as a rubber or elastomer, may be provided between eye divider 20 and bearing surface 33 to generate the desired friction there between.

Figure 6:
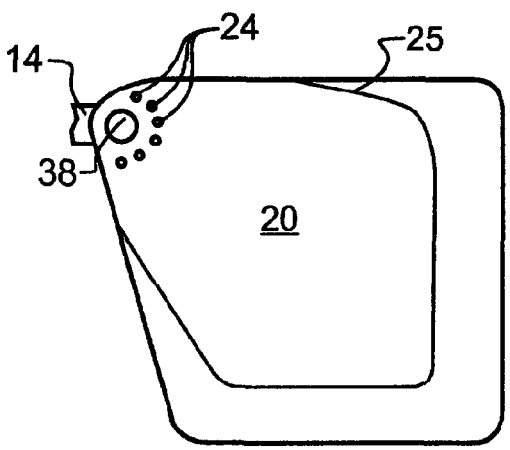
FIG. 6 illustrates the exemplary coupling between eye divider and frame used in the first preferred embodiment baseball training apparatus of FIG. 1, from an enlarged side elevation view.

Coupling 30, illustrated in detail in FIGS. 5 and 6, enables a person to remove eye divider 20 if so desired. This permits a player 1 to remove and replace eye divider 20 with a similar divider of different geometry. In accord with the methods of the invention, a player 1 may then select how far eye divider 20 extends from the player's nose 4, the slope relative to their nose 4, and other eye divider 20 dimensions or proportions by selecting one particular geometry eye divider 20 selected from a variety of eye dividers 20, each having different geometries. This selection may be made at any time, including immediately before or during a particular use or practice session.

Figure 3:
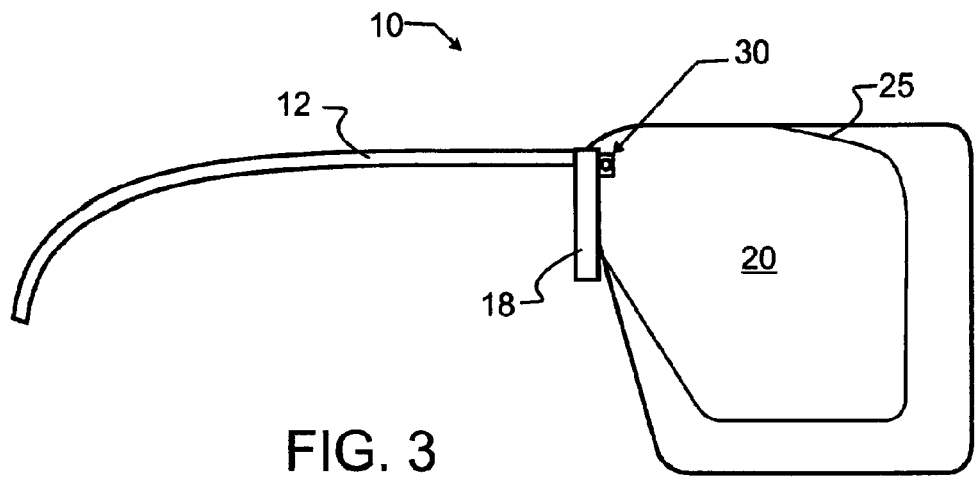
FIG. 3 illustrates the first preferred embodiment baseball training apparatus of FIG. 1 from a side elevation view, and having a preferred eye divider in a first position.
Figure 4:
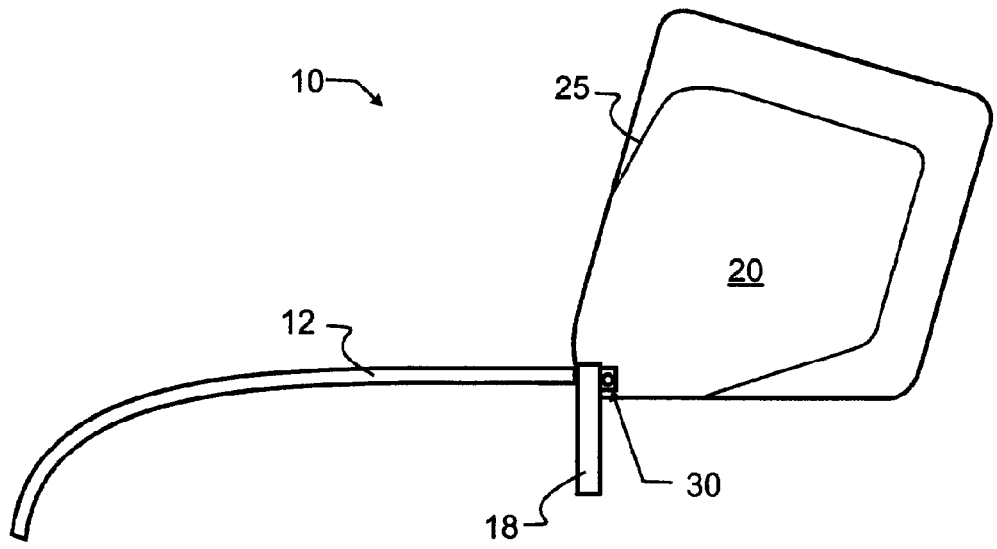
FIG. 4 illustrates the first preferred embodiment baseball training apparatus of FIG. 1 from a side elevation view, and having the preferred eye divider in a second position.

In an alternative embodiment, eye divider 20 may be provided with one or more scribes therein, such as scribe 25 illustrated in FIG. 3. The purpose of scribe 25 is to allow a player 1 to break off and dispose of the portion of eye divider 20 exterior to scribe 25, should player 1 desire a smaller or differently shaped eye divider. The number and placement of scribes 25 is essentially unlimited, and can be used to accommodate players of different sizes or preferences, or having noses 4 of different geometry, or for any other reason.

Figure 7:
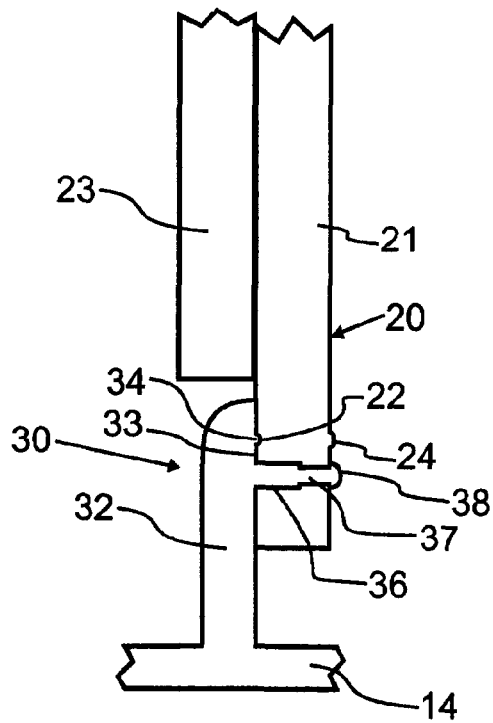
FIG. 7 illustrates an alternative eye divider from the sectional view of FIG. 5.

In yet another alternative, eye divider 20 may be intrinsically extendible, or may be provided on a support or mount that permits eye divider 20 to be moved generally parallel to the sagittal plane, such that eye divider 20 may be moved farther from or closer to eyes 2,3 and nose 4. The purpose of making eye divider 20 extendible is similar to the provision of scribes 25, permitting adjustment to be made by a player 1. However, unlike scribes 25, such adjustment, if designed accordingly, could be made at any time by player 1. For exemplary purposes, and not limited solely thereto, eye divider 20 may be made intrinsically extendible by fabricating eye divider 20 not from a single sheet of material, but from two or more layers 21, 23 as illustrated in FIG. 7. The layers may be held together with any suitable coupling technique including but not limited to hook and loop fasteners, tapes and adhesives, holes and protrusions similar to holes 16, or other fasteners. Layer 21 is coupled directly to coupling 30, while layer 23 is supported solely by and may be extended along layer 21, such that layer 23 may then be adjusted relative to layer 21 to extend farther from nose 4.

In a further alternative, eye divider 20 may take on dimensions other than the generally planar, sheet form such as illustrated in FIG. 2, and so may, for exemplary purposes only and not limiting thereto, take on the shape of a V when viewed from above as in FIG. 2, with the point of the V distal to eyes 2, 3 and nose 4, thereby essentially mimicking the shape of nose 4 from that top view but extending nose 4 by a desired amount.

Figure 8:
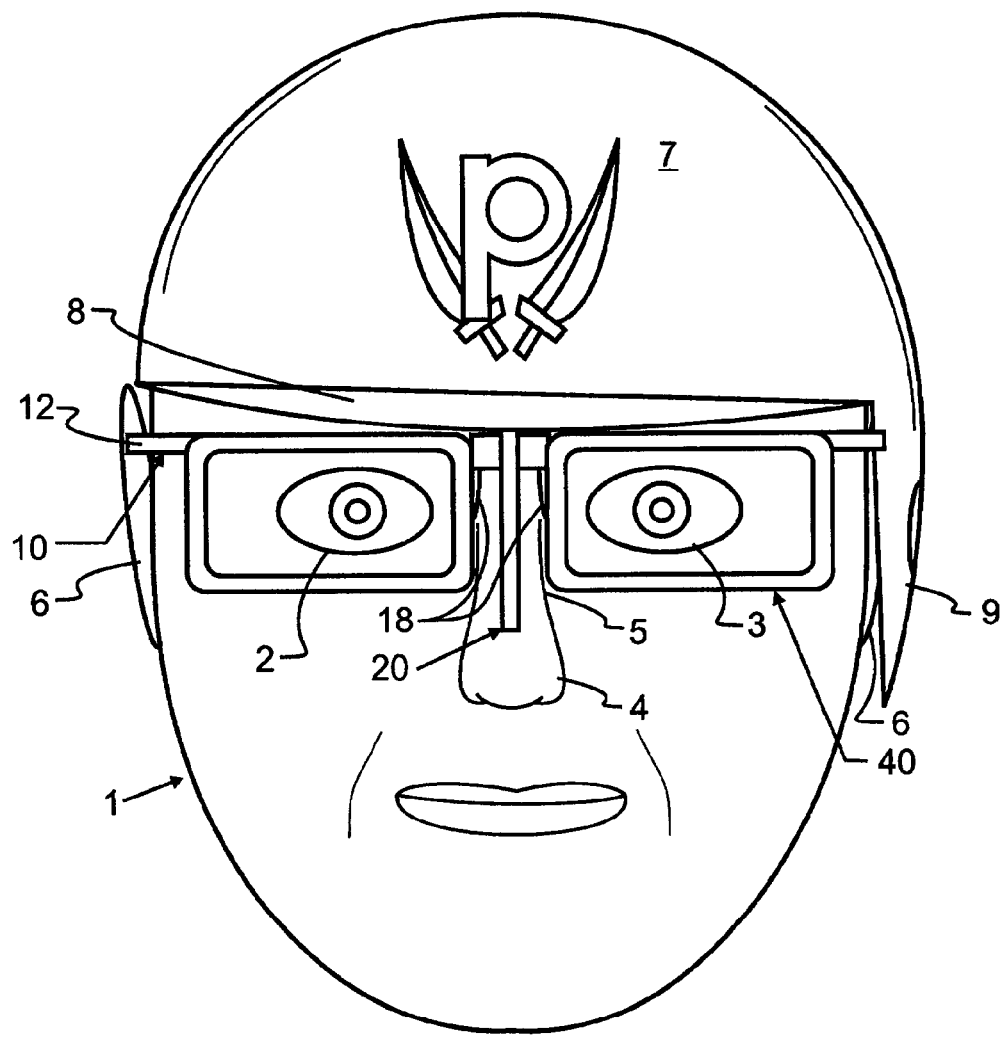
FIG. 8 illustrates a second preferred embodiment baseball training apparatus designed in accord with the teachings of the present invention.
Figure 9:
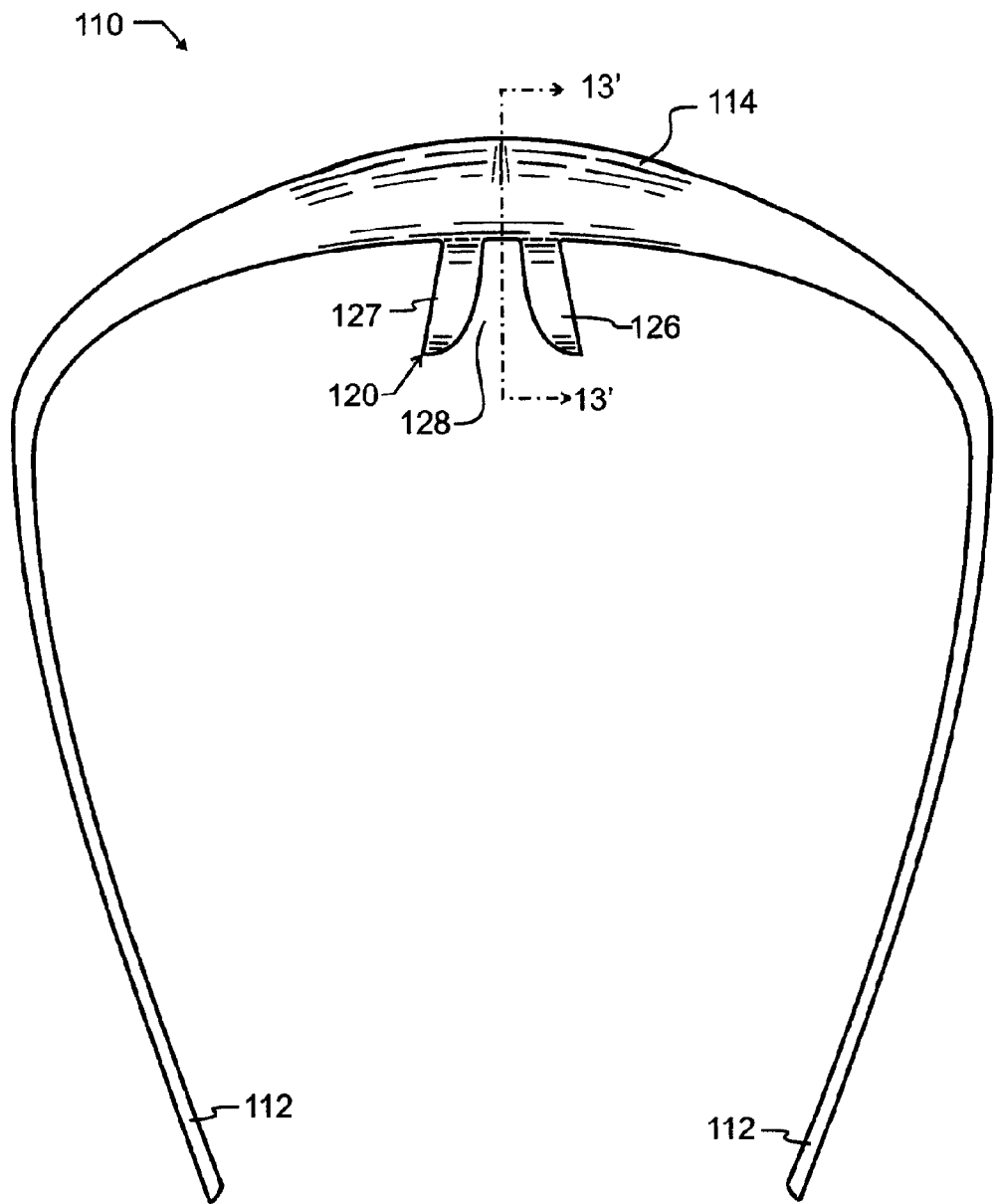
FIG. 9 illustrates a third preferred embodiment baseball training apparatus designed in accord with the teachings of the present invention from a to plan view.

FIG. 8 illustrates a second preferred embodiment baseball training apparatus 10, which otherwise resembles that of FIG. 1 but with the addition of eye frames 40. These frames may be fabricated integrally with top bar members 14, or may have protrusions suitable to be press fit into holes 16. Suitable protrusions provided on temples 12 and eye frames 40 might, for exemplary purposes only and not limiting thereto, comprise a shaft terminated by a slightly bulbous end, resembling a pin with a round pin head. The bulbous portion would preferably pass just through a hole 16, with the shaft remaining in the hole 16 and having a diameter similar thereto. Eye frames 40 may optionally be provided with clear, tinted, polarized, corrective, or otherwise treated eye pieces, as may be desired for beneficial function or aesthetic or ornamental appearance.

FIGS. 9-14 illustrates a third preferred embodiment baseball training apparatus 110, which retains many of the features found in the first preferred embodiment baseball training apparatus 10 of FIG. 1. This third preferred embodiment is distinguished from the earlier embodiments by the hundreds digit, and various components within each embodiment designated by the ones and tens digits. However, many of the components are alike or similar between embodiments, so numbering of the ones and tens digits have been maintained wherever possible, such that identical, like or similar functions may more readily be identified between this third preferred embodiment and the previous embodiments. If not otherwise expressed, those skilled in the art will readily recognize the similarities and understand that in many cases like numbered ones and tens digit components may be substituted from one embodiment to another in accord with the present teachings, except where such substitution would otherwise destroy operation of the embodiment. Consequently, those skilled in the art will readily determine the function and operation of many of the components illustrated herein without unnecessary additional description.

Figure 10:
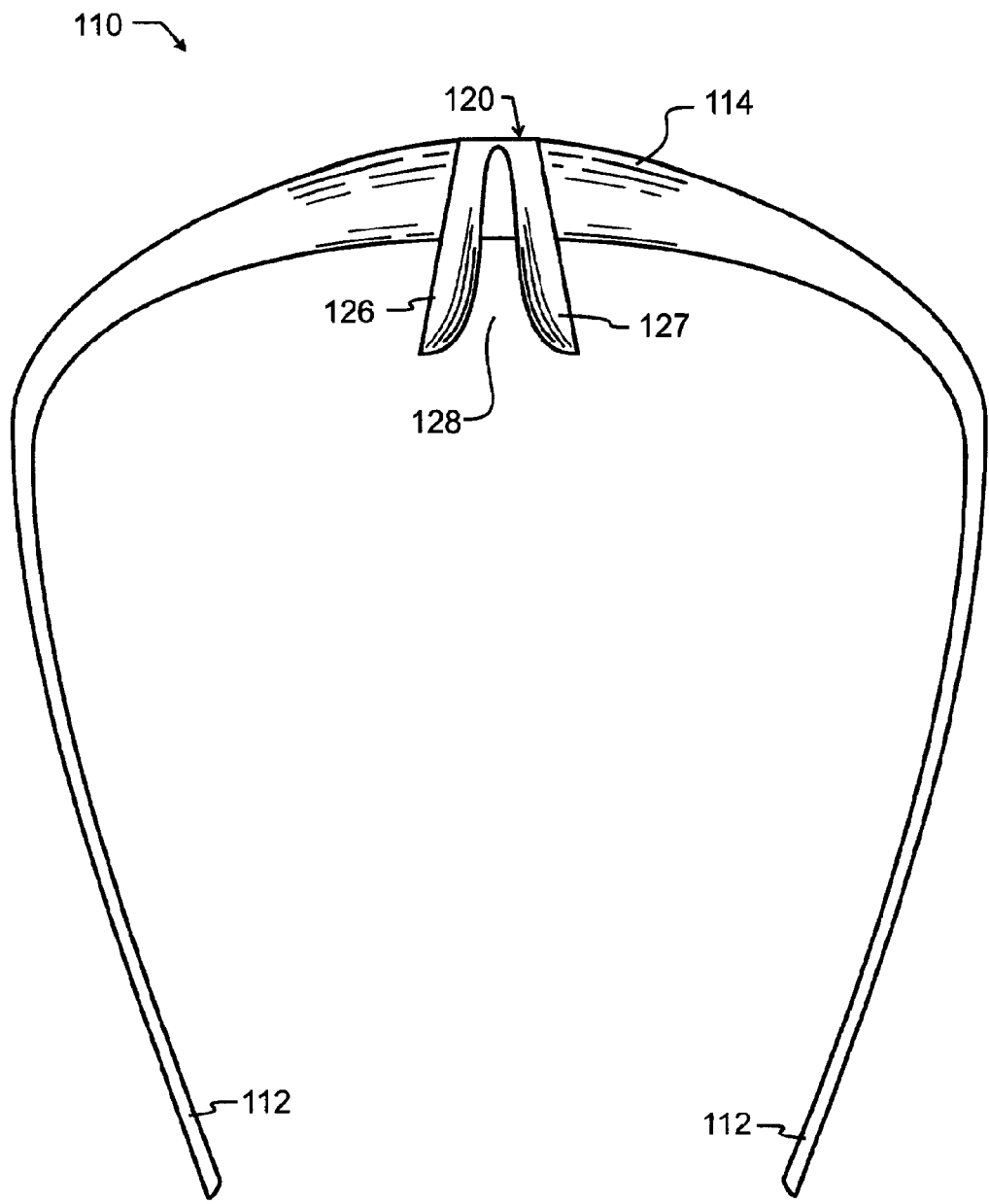
FIG. 10 illustrates the third preferred embodiment baseball training apparatus of FIG. 9 from a bottom plan view.

In this third preferred embodiment baseball training apparatus 110, eye divider 120 takes the shape of a V when viewed from above or below, such as in FIG. 10. Right divider 126 and left divider 127 are separated by a small gap 128 within which nose bridge 5 will operatively extend. The point of the V, where right divider 126 and left divider 127 converge, is distal to eyes 2, 3, and nose 4, as visible in FIG. 14. Consequently, eye divider 120 essentially mimics the shape of nose bridge 5 from top and bottom views but extends outward from nose 4 by a desired amount.

Eye divider 120 has a large surface area relative to thickness, and the outer surfaces of right divider 126 and left divider 127 extend generally along or substantially parallel to the sagittal anatomical plane to divide the player's face into right and left halves. While these outer surfaces are slightly offset from the sagittal anatomical plane, too great an offset will either cause eye divider 120 to become very large and potentially interfering with forward vision, or will shorten the distance away from bridge 5 in the direction of the pitcher that eye divider 120 extends, potentially becoming too short to be functionally effective. Consequently, the outer surfaces will only be minimally offset from parallel to the sagittal plane.

In this third preferred embodiment baseball training apparatus 110, the inner surfaces of right divider 126 and left divider 127 that define small gap 128 are tapered or angled, to together form a generally V-shaped opening. As a result, eye divider 120 eliminates the need for a separate nose piece, and is instead preferably designed to rest on nose bridge region 5, and together with temples 112 support the balance of baseball training apparatus 110 upon baseball player 1. Small gap 128 may take on any of the many geometries known in the glasses art for nose pieces, and the present invention is not limited by one or another design. The exact shape of small gap 128 is not critical to the invention, but will preferably be designed for reasonable comfort and hold when worn by a baseball player 1.

For both safety and aesthetic reasons, a pair of temples or legs 112 are smoothly and integrally formed extensions of frame or top bar member 114. Most preferably, top bar member 114 is relatively thin, having a top and bottom surface that are both generally planar and defined substantially within adjacent transverse anatomical planes, such as evidenced by FIGS. 11 and 12, extending only slightly vertically. Within this horizontal transverse plane, such as evidenced by FIGS. 9 and 10, top bar member 114 is substantially wider. This provides desired strength with minimal material consumption and weight, and is extremely complementary to both temples 112 and eye divider 120. In addition, the geometry is quite complementary with a helmet, since frame 114 extends parallel to the bill of the helmet. While not normally required since most baseball players wear a helmet, frame member 114 will also serve as a nominal sun shield. Finally, frame 114 will also provide some limited visual restriction in a vertical direction, in the event the player is not wearing a helmet or billed cap that would do likewise. In other words, frame member 114 will block vision in a direction towards the top of the player's head, thereby assisting not only with left-right orientation, but also upward orientation, again training the player to look directly at the pitcher.

As visible in FIG. 12, there is preferably a slight arc 115 out of the transverse plane such that the portion of frame more distal to player 1 curves slightly downward towards the player's feet. This slight curvature 115 preferably provides slight but important controlled flexure in the event of a direct baseball impact.

Temples 112 are preferably fabricated from a resilient material, and provided with sufficient curvature that the ends of temples 112 distal to top bar member 114 are closer to each other than the ends adjacent. This combination of the free ends of temples 112 being closer together and providing resilience in temples 112 allows the temples to gently squeeze or hold on a person's head. Good materials selection and design may eliminate the need for adjustable connection. It is therefore further contemplated that the preferred baseball training apparatus 110 might, for exemplary purposes only and not limiting the present invention thereto, be provided in only a few sizes, such as a child's size and an adult size, where differences of wearers within the size ranges are fully accommodated by the resilience of temples 112.

Figure 13:
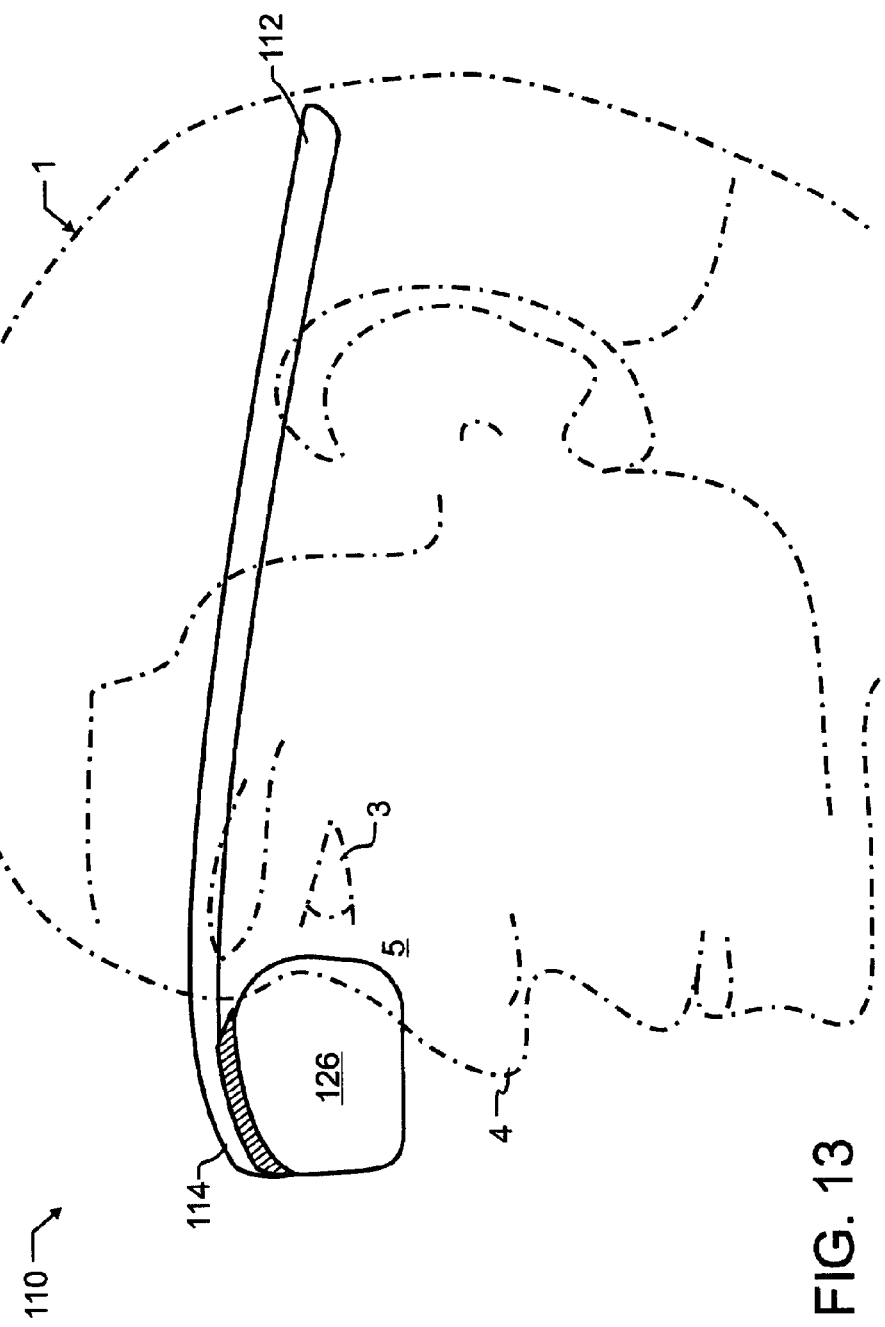
FIG. 13 illustrates the third preferred embodiment baseball training apparatus from a side sectional view taken along section line 13' of FIG. 9 and further illustrates a person operatively wearing the third preferred embodiment baseball training apparatus.
Figure 14:
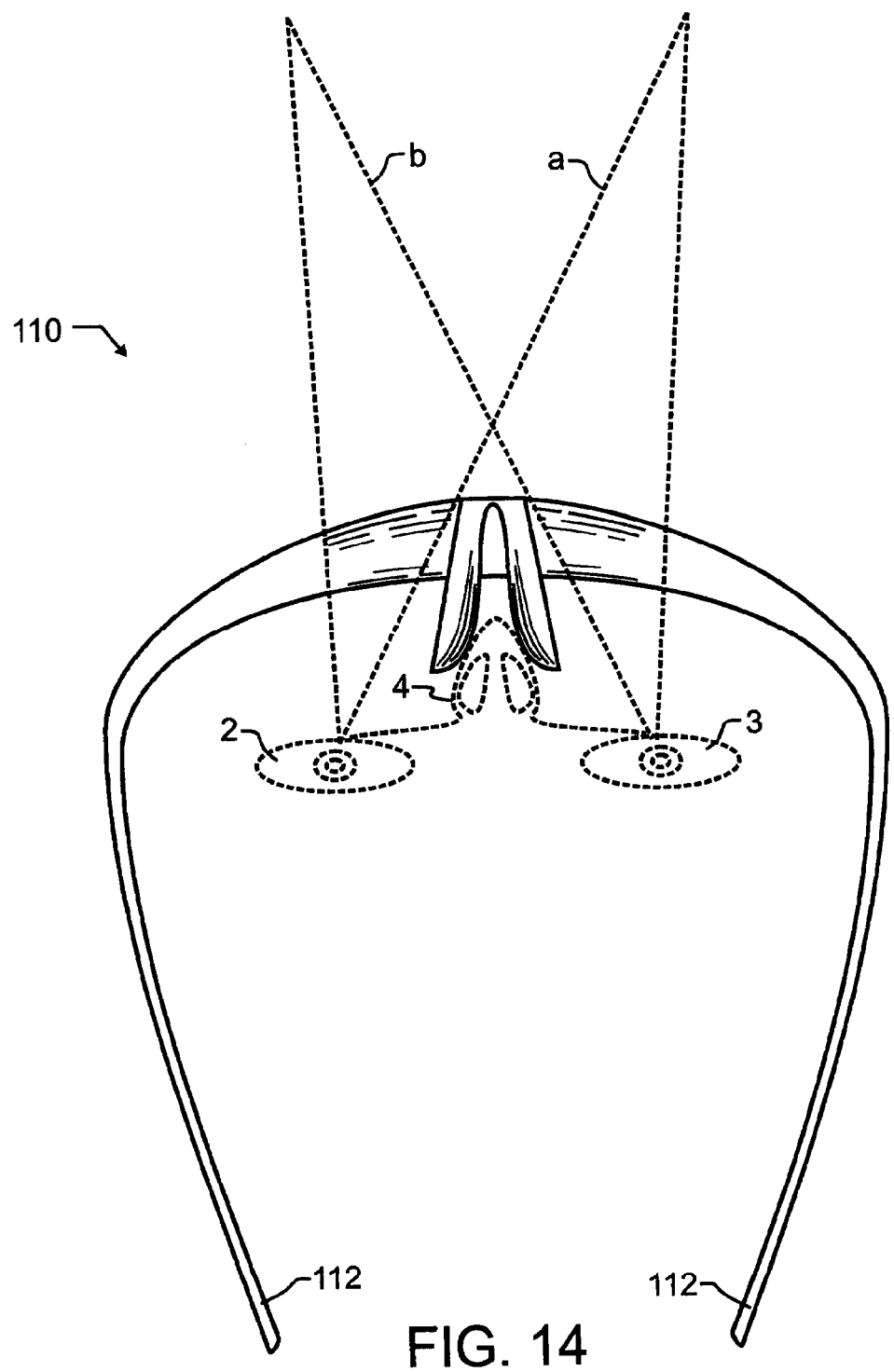
FIG. 14 illustrates the third preferred embodiment baseball training apparatus of FIG. 9 from a bottom plan view and further illustrates a person's eyes and nose, and the viewing angle obtained by operatively wearing the third preferred embodiment baseball training apparatus.

As illustrated in FIG. 14, an exemplary prior art baseball player has vision from right eye 2 and left eye 3. Player 1 has a nose 4 that extends to the bridge region 5 between right eye 2 and left eye 3. A baseball player 1 will most desirably position so that right eye 2 and left eye 3 are facing directly at a pitcher or incoming baseball. To enable baseball player 1 to confirm that eyes 2, 3 are, in fact, directly facing the pitcher, baseball training apparatus 110 is adapted to be operatively placed on the player's face as shown in FIG. 13. If right eye 2 in FIG. 14 were to be closer to the pitcher or incoming baseball than left eye 3, then the farthest right line of sight from left eye 3, designated by line b in the figure, would become blocked by eye divider 120, such that the baseball or pitcher would no longer be visible through left eye 3. Similarly, if player 1 has his head shifted the other direction, then the baseball or pitcher would no longer be visible through right eye 2 along leftmost line of sight a. The various training methods described herein above with regard to the previous embodiments are equally applicable to preferred baseball training apparatus 110.

Not all players will have the same nose geometry, yet, preferably, eye divider 120 will be placed or positioned immediately adjacent to nose 4. A gap there between can allow a batter to see with the back eye between eye divider 120 and nose 4, thereby rendering eye divider 120 ineffective or less beneficial. For the purposes of the present disclosure, eye divider 120 will be understood to be immediately adjacent to nose 4 when any gap there between is sufficiently small to substantially prevent clear or unobstructed vision there between. Most preferably, this is best ensured by making small gap 128 large enough to at least partially wrap about nose bridge 5.

Most preferably, baseball training apparatus 10 will be fabricated from materials that are safe for the application. Preferred materials are semi-rigid such that they maintain shape during ordinary and intended use, but that, in the event of an impact from a ball or other object, the material will deform without harming the player. Exemplary materials include, but are not limited to, elastomers, rubber, foam, certain plastics, composites, and laminates. Reinforcing or shape maintaining materials may be provided to help maintain structural integrity or shape. Finally, the components will preferably be free of dangerous edges or significant protrusions that might harm a player, in the event the player were to be wearing baseball training apparatus 10 and be struck by a ball or other object.

While the foregoing details what is felt to be the preferred embodiment of the invention, no material limitations to the scope of the claimed invention are intended. Further, features and design alternatives that would be obvious to one of ordinary skill in the art are considered to be incorporated herein. For exemplary purpose, the preferred and alternative embodiments illustrated herein are mounted upon a frame similar to eyeglasses. However, the structure supporting the eye divider 20 is not critical to the invention, and might, for exemplary purposes, include a batting helmet, baseball cap, or other head covering or attachment. While the present invention is described with specific reference to baseball, for the purposes of the present disclosure baseball will be understood to include closely related sports such as softball that have a pitcher and hitter, where the hitter will orient their shoulders askance to the pitcher but must still properly view pitcher and pitch. The scope of the invention is set forth and particularly described in the claims herein below.

I claim:

1. A baseball training apparatus for assisting a baseball player in keeping their head aligned with an object, comprising:

a frame defining a forward portion of said baseball training apparatus extending longitudinally between distal ends substantially within a coronal anatomical plane and defining top and bottom generally planar major surfaces each of said top and bottom planar major surfaces substantially within a transverse anatomical plane;

a pair of temples each extending generally perpendicularly from a one of said distal ends of said frame body support adapted to operatively couple said baseball training apparatus to said baseball player; and an eye divider coupled with and extending both downward and posterior from said frame bottom generally planar major surface and having right and left dividers that each have a major surface extending substantially parallel to a sagittal anatomical plane, said right and left dividers separated by a gap at a first termination distal to said frame and defining a nose bridge region, and converging adjacent to said frame and distal to said nose bridge region, said nose bridge region adapted to operatively couple partially about a nose bridge of said baseball player.

2. The baseball training apparatus for assisting a baseball player in keeping their head aligned with an object of claim 1, wherein said frame top and bottom planar major surfaces further comprise a curvature out of the transverse plane adapted to operatively provide controlled flexure in the event of a direct baseball impact.

3. The baseball training apparatus for assisting a baseball player in keeping their head aligned with an object of claim 1, wherein said nose bridge region is adapted to operatively prevent clear vision between said nose bridge region and said nose bridge of said baseball player.

4. A baseball training apparatus for assisting a baseball player in keeping their head aligned with an object, comprising:

a frame defining a forward portion of said baseball training apparatus extending longitudinally between distal ends substantially within a coronal anatomical plane;

a pair of temples each extending generally perpendicularly from a one of said distal ends of said frame body support and adapted to operatively couple said baseball training apparatus to said baseball player; and an eye divider unitary with and extending both downward and posterior from said frame bottom generally planar major surface and having right and left major surfaces extending substantially parallel to a sagittal anatomical plane, said right and left major surfaces separated by a gap at a first termination distal to said frame defining a nose bridge region, and converging adjacent to said frame and distal to said nose bridge region, said nose bridge region adapted to operatively couple partially about a nose bridge of said baseball player.

5. The baseball training apparatus for assisting a baseball player in keeping their head aligned with an object of claim 4, wherein said frame further comprises top and bottom generally planar major surfaces each substantially within a transverse anatomical plane.

6. The baseball training apparatus for assisting a baseball player in keeping their head aligned with an object of claim 5, wherein said frame top and bottom planar major surfaces further comprise a curvature out of said the transverse anatomical plane adapted to operatively provide controlled flexure in the event of a direct baseball impact.

7. The baseball training apparatus for assisting a baseball player in keeping their head aligned with an object of claim 4, wherein said nose bridge region is adapted to operatively prevent clear vision between said nose bridge region and said nose bridge of said baseball player.

8. The baseball training apparatus for assisting a baseball player in keeping their head aligned with an object of claim 4, wherein said eye divider extends vertically from adjacent an eyebrow of said baseball player to below an eye of said baseball player.

\* \* \* \* \*